United States Patent
Honeit et al.

(10) Patent No.: US 9,605,155 B2
(45) Date of Patent: Mar. 28, 2017

(54) GOLD PIGMENT

(71) Applicant: Merck Patent GmbH, Darmstadt (DE)

(72) Inventors: Ute Honeit, Darmstadt (DE); Sylke Klein, Rossdorf (DE)

(73) Assignee: Merck Patent GmbH, Darmstadt (DE)

( * ) Notice: Subject to any disclaimer, the term of this patent is extended or adjusted under 35 U.S.C. 154(b) by 74 days.

(21) Appl. No.: 14/425,143

(22) PCT Filed: Aug. 16, 2013

(86) PCT No.: PCT/EP2013/002471
§ 371 (c)(1),
(2) Date: Mar. 2, 2015

(87) PCT Pub. No.: WO2014/037079
PCT Pub. Date: Mar. 13, 2014

(65) Prior Publication Data
US 2015/0259538 A1 Sep. 17, 2015

(30) Foreign Application Priority Data

Sep. 6, 2012 (DE) ......................... 10 2012 017 608

(51) Int. Cl.
| | | |
|---|---|---|
| *C09D 11/037* | (2014.01) | |
| *C09D 5/36* | (2006.01) | |
| *C09C 1/24* | (2006.01) | |
| *C09C 1/36* | (2006.01) | |
| *C09C 3/06* | (2006.01) | |
| *C09C 1/00* | (2006.01) | |
| *A61K 8/29* | (2006.01) | |
| *A61Q 1/00* | (2006.01) | |
| *A61Q 1/02* | (2006.01) | |
| *A61K 8/19* | (2006.01) | |
| *C09D 11/02* | (2014.01) | |

(52) U.S. Cl.
CPC ............... *C09C 3/063* (2013.01); *A61K 8/19* (2013.01); *A61K 8/29* (2013.01); *A61Q 1/00* (2013.01); *A61Q 1/02* (2013.01); *C09C 1/0015* (2013.01); *C09C 1/0021* (2013.01); *C09C 1/0039* (2013.01); *C09D 5/36* (2013.01); *C09D 11/02* (2013.01); *A61K 2800/436* (2013.01); *C01P 2004/54* (2013.01); *C01P 2004/61* (2013.01); *C01P 2006/62* (2013.01); *C01P 2006/63* (2013.01); *C01P 2006/64* (2013.01); *C01P 2006/65* (2013.01); *C01P 2006/66* (2013.01); *C09C 2200/102* (2013.01); *C09C 2200/1004* (2013.01); *C09C 2200/301* (2013.01); *C09C 2200/302* (2013.01); *C09C 2220/10* (2013.01)

(58) Field of Classification Search
CPC ....... C09D 11/037; C09D 5/36; C09C 1/0015; C09C 1/0021; C09C 1/0024; C09C 1/0039; C09C 2200/1004; C09C 2200/102; C09C 2200/301; C09C 2200/302; C09C 2200/10; C01P 2004/54; C01P 2004/61; C01P 2006/62; C01P 2006/63; C01P 2006/634; C01P 2006/65; C01P 2006/66
USPC .................. 106/31.9, 439, 456; 427/214
See application file for complete search history.

(56) References Cited

U.S. PATENT DOCUMENTS

| | | | |
|---|---|---|---|
| 5,009,711 A | | 4/1991 | Emmert et al. |
| 5,607,504 A | * | 3/1997 | Schmid .................... C09D 5/36 106/456 |
| 5,702,519 A | * | 12/1997 | Nitta .................... C09D 11/037 106/442 |
| 5,958,125 A | * | 9/1999 | Schmid ................. C09C 1/0015 106/439 |
| 6,579,355 B1 | | 6/2003 | Schmidt et al. |
| 6,599,355 B1 | | 7/2003 | Schmidt et al. |
| 6,689,205 B1 | | 2/2004 | Bruckner et al. |
| 6,692,561 B1 | | 2/2004 | Schoen et al. |
| 7,169,222 B2 | | 1/2007 | Bruckner et al. |
| 2004/0144023 A1 | | 7/2004 | Bruckner et al. |
| 2005/0241530 A1 | | 11/2005 | Bruckner et al. |
| 2010/0116169 A1 | | 5/2010 | Kaupp et al. |

FOREIGN PATENT DOCUMENTS

| | | |
|---|---|---|
| DE | 19618569 A1 | 11/1997 |
| DE | 19915153 A1 | 8/2000 |
| DE | 19951869 A1 | 5/2001 |
| DE | 19951871 A1 | 5/2001 |
| EP | 0307747 A1 | 3/1989 |
| EP | 0763573 A2 | 3/1997 |
| EP | 1029900 A1 | 8/2000 |
| EP | 1980594 A1 | 10/2008 |
| WO | 01/30921 A1 | 5/2001 |

OTHER PUBLICATIONS

English translation of the Written Opinion of the International Search Authority mailed Mar. 10, 2015 for PTC/EP2013/002471; 12 pages.*
International Search Report from PCT Application No. PCT/EP2013/002471 dated Dec. 2, 2013.

* cited by examiner

*Primary Examiner* — Helene Klemanski
(74) *Attorney, Agent, or Firm* — Millen White Zelano and Branigan, PC; John Sopp; Anthony Zelano

(57) ABSTRACT

The present invention relates to a golden interference pigment which is suitable, in particular, for printing processes, to a process for the preparation of a pigment of this type, and to the use thereof.

20 Claims, No Drawings

GOLD PIGMENT

The present invention relates to golden interference pigments, in particular golden interference pigments which have at least one layer comprising $Fe_2O_3$ and $TiO_2$ on a specific substrate and which are suitable for printing processes, to a process for the preparation thereof, and to the use thereof.

Golden or gold-coloured articles have always been associated with the impression of beauty, value and exclusivity. The essential difference between the colours "yellow" and "gold" in principle consists merely of the lustre which is additionally associated with the gold shade and which ultimately attracts attention and desire.

Products which are intended to promote exclusivity and luxury have therefore for a long time been provided with packaging or decoration which more or less imitates the appearance of pure gold. Besides the many requirements nowadays made of modern packaging and the like, for example low levels of or freedom from harmful substances, good recycling possibilities and/or favourable raw materials, there is also an increasing demand, in particular, for simple, fast and inexpensive production processes for the production of the end products, for example packaging materials. Coating processes, in particular printing processes, therefore come into consideration for the production of packaging, decoration or also security products.

Gold-coloured decorations are therefore increasingly being applied to the respective substrates by means of coating and printing processes. However, each of the coating processes requires, for technological reasons, different properties of the pigments present in each case which characterise the optical appearance. Lustre effects similar to a gold lustre cannot be obtained using pure absorption pigments, meaning that so-called effect pigments are usually employed for this purpose. These generally consist, if they are interference pigments, of transparent flake-form support materials which are covered with one or more thin layers of various materials, usually metal oxides, where the optical interaction of support and coating results in interference effects and, besides interference colours, lustre is also produced.

However, it has been found that flake-form effect pigments, depending on their particle size, either increasingly produce lustre and glitter effects in the application medium, which is the case for relatively large particle sizes, or alternatively, in the case of relatively small particle sizes, comparatively good hiding power can be achieved, even in the case of effect pigments which are essentially transparent per se. However, these effects are mutually contradictory, meaning that compromises must always be made between desired lustre and likewise desired high hiding power on use of interference pigments.

At the same time, the various printing processes likewise only allow certain particle sizes of solids employed, meaning that, in particular in the case of printing processes which can only be carried out with very finely divided pigments, for example the offset printing process and the intaglio printing process, there is virtually no possibility of being able to achieve any significant lustre at all using conventional finely divided effect pigments. In addition, the layer thicknesses that can be achieved are very thin, in particular in the case of the offset process, which in turn reduces the colour effects, in particular the colour saturation, that can be achieved using effect pigments.

In addition, cold, greenish yellow shades are not perceived by the human eye as "proper" yellow or gold. This tends to be more the case for warm, slightly reddish yellow shades. In addition, the usual gold-effect pigments often exhibit very high brightness values, meaning that although printed images produced therewith appear gleamingly bright at the specular angle, they do not appear in a saturated gold shade.

Gold-coloured effect pigments which are based on interference appearances are known in some variety. They are generally based on natural or synthetic mica, glass flakes or $SiO_2$ flakes and have interference layers, which may consist, inter alia, of $TiO_2$, of $Fe_2O_3$ or of mixtures of the two metal oxides.

Thus, for example, DE 196 18 569 A1 discloses multi-layered interference pigments which have a layer system comprising alternating high- and low-refractive-index materials on a transparent support material. If the high-refractive-index layers comprise $Fe_2O_3$, pigments having an orange-red mass tone and possibly interference colours in the similar colour spectrum are obtained.

DE 199 15 153 A1, DE 199 51 871 A1 and DE 199 51 869 A1 each describe intensely coloured interference pigments which have multilayered systems on a transparent support material, where at least one of the layers comprises a mixture of $TiO_2$ and $Fe_2O_3$ or pseudobrookite. The lustre pigments obtained have mass tones in the orange-red region and/or a usually greenish-golden interference. The examples show pigments based on mica having a particle size of 10-60 μm.

The mica-based pigments described in the prior art are not suitable or not very suitable for specific printing processes, such as, for example, offset printing or intaglio printing, merely owing to their particle sizes, since they inadequately fill or clog the printing plates or cannot align correctly in the application medium. If they are employed in relatively small particle sizes in printing processes of this type, the achievable hiding power and in particular the lustre is, by contrast, not sufficient in order to produce the desired saturated, lustrous gold shade. This aim also cannot be achieved with the predominantly greenish gold shades.

The object of the present invention is therefore to provide a golden interference pigment which has an interference-capable coating on a transparent support material and exhibits, both in the mass tone and also in the interference colour, a warm, strong reddish gold shade which is independent of the viewing angle, high lustre and high hiding power, is suitable for virtually all common printing processes and in the application medium results in saturated, warm, lustrous gold shades in the print images obtained.

The object of the present invention is furthermore to provide a process for the preparation of a golden interference pigment of this type.

A further object of the invention consists in indicating the use of the interference pigments according to the invention.

The object of the present invention is achieved by a golden interference pigment which comprises a flake-form substrate and at least one layer located on the substrate, where the flake-form substrate is a transparent, synthetically produced substrate which has per se a green inherent interference colour, where at least one layer which comprises a mixture or mixed oxide of $Fe_2O_3$ and $TiO_2$ is located on the substrate.

The object of the present invention is furthermore achieved by a process for the preparation of the golden interference pigment according to the invention in which a synthetically produced transparent substrate which has a green inherent interference colour is covered with at least one layer which comprises a mixture or mixed oxide of $Fe_2O_3$ and $TiO_2$.

The object of the invention is likewise achieved by the use of the golden interference pigment according to the invention in paints, coatings, printing inks, plastics, glasses, paper, ceramic, cosmetic formulations, for the laser marking of plastics or paper and for the preparation of pigment preparations and dry preparations.

The substrate which is used for the preparation of the golden interference pigment according to the invention is a transparent, synthetically produced flake-form substrate which per se already has a green inherent interference colour.

A substrate flake is regarded as transparent in the sense of the present invention if it essentially, i.e. to the extent of at least 80%, transmits incident visible light. In addition, the substrate flakes employed in accordance with the invention do not have an absorption colour.

The substrate flakes employed in accordance with the invention are synthetically produced flake-form substrates of homogeneous composition which have an upper surface and a lower surface which form the principal surfaces of the respective flake and are arranged parallel to one another. Parallel in the sense of the present invention means not only parallel in the geometric sense, but also encompasses deviations in the positioning of the surfaces to one another compared with geometrical parallelism of up to 15°. The length or width of these principal surfaces of the respective substrate flake represents the particle size of the substrate flake in its respective longest dimension, while the average separation between the substrate surfaces represents the geometrical thickness of the respective substrate flake and the averaged thickness of all substrate flakes represents the geometrical thickness of the substrates.

Furthermore, the synthetically produced flake-form substrates employed in accordance with the invention have planar and very smooth surfaces. Due to the synthetic production of the substrate flakes, the surface properties, the geometrical thickness, the particle size and in the best case also the particle size distribution can be precisely controlled and set by means of the process parameters during the production of the substrate flakes, which cannot be ensured in the case of natural materials, such as, for example, mica, talc or kaolin, which are usually likewise used as substrate materials for interference pigments.

Due to the very planar, parallel surfaces of the substrate flakes, their homogeneous composition and the absence of an absorption colour, the substrate flakes in a clear, transparent medium surrounding them having a refractive index which is different from the flakes reflect at least 5% and up to 20%, in particular 6 to 20%, of the incident visible light, depending on the respective refractive index of the flakes. The reflected proportion of light here is greater the higher the refractive index of the respective flake material employed. This reflection at the respective interfaces with the ambient medium results, in combination with the path difference arising, in interference of the reflected light beams and thus in an inherent interference colour of the substrate flakes.

The substrate flakes employed in accordance with the invention have a green inherent interference colour (light in the wavelength range from 490 to 550 nm), which is determined on the basis of the diffuse reflection or the total reflection of the substrate flakes in a transparent, colourless medium.

In order to determine this inherent interference colour, a Hunter L,a,b diagram is determined from the diffuse reflection determined with the aid of a corresponding Ulbricht sphere or the total reflection of incident visible light (sample: coating with a thickness of 10 μm on transparent PET film, comprising a commercially available transparent, colourless gravure printing binder and 10% by weight of substrate flakes). The reflection values for the substrate flakes according to the invention in the Hunter L,a,b diagram here are in each case in the range L>30, in particular L=40 to 80, b=−20 to +20, in particular −10 to +10, and a<0, in particular a=−0.1 to −20, particularly preferably −0.1 to −10.

Conventional pigment substrates have either no or no predominantly visible and measurable monochrome interference colour. Thus, mica flakes, irrespective of whether they are based on natural or synthetically produced mica, are not per se capable of interference of this type, which manifests itself as a uniformly perceptible, predominant, monochrome interference colour, owing to their layer-wise structure of silicate layers and the consequently non-planar surfaces. Instead, mica flakes shimmer in various colours depending on the viewing angle in the case of a relatively large layer thickness, which results in a whitish, undefined overall colour impression in the case of a loose bed of pure mica flakes.

Under the prerequisite that the substrate flakes have planar and parallel substrate surfaces, the optical properties of the substrates employed in accordance with the invention are essentially determined by the refractive index of the substrate material and by the geometrical thickness of the substrate.

Due to the content of any foreign oxides present, but also due to included pores or depending on the crystal modification of the metal oxides preferably employed, the refractive index of the substrate material here may in some cases differ from the ideal refractive index of the pure substrate materials (bulk material, measured under standard conditions, for example by the Landoll-Börnstein method), meaning that the geometrical layer thickness of the substrates must be adapted correspondingly, depending on the production conditions and material used, in order to achieve the desired interference colour.

In order to be able to obtain substrate thicknesses which are suitable for pigment preparation, the refractive index n of the substrate material should be at least greater than 1.5 and preferably at least 1.65. Suitable materials for the substrate are therefore dielectric materials or material mixtures in which the material or material mixture in each case has a refractive index n of greater than 1.5, preferably of at least 1.65.

Preference is given to colourless materials or material mixtures.

It is furthermore necessary for the substrate of the golden interference pigment according to the invention to have a refractive index $n_1$ which has a separation $\Delta n$ from the refractive index $n_2$ of an interference layer to be applied to the substrate of at least 0.1, better at least 0.2.

Suitable materials for the substrate of the interference pigment according to the invention are therefore, in particular, colourless metal oxides or also specific glass materials having a refractive index n in the range from >1.5 to 2.5, in particular from 1.65 to 2.5.

Particularly preferably suitable as substrate are substrate flakes which consist of $Al_2O_3$, of $Al_2O_3$ with a content of up to 5% by weight of $TiO_2$, based on the weight of the substrate, of $ZrO_2$ or of $TiO_2$, or substrate flakes which comprise $Al_2O_3$, $ZrO_2$ or $TiO_2$ with a proportion of at least 90% by weight, based on the weight of the substrate. $TiO_2$ here may be in the anatase or rutile modification.

Further constituents of the transparent substrate flakes may be the oxides or oxide hydrates of Sn, Si, Ce, Al, Ca, Zn and/or Mg, which, however, are present in the substrate at most with a proportion of 10% by weight, based on the weight of the substrate, and do not essentially determine the optical properties, in particular the interference colour, of the substrate.

Suitable as substrate material are also glass flakes which meet the requirements of the refractive index. This is the case, in particular, for flakes comprising glass material whose proportion of $SiO_2$ is at most 70% by weight. In addition, glass materials of this type also comprise contents of $Al_2O_3$, CaO, MgO, $B_2O_3$, $Na_2O$, $K_2O$, $TiO_2$, ZnO, BaO, $Li_2O$, $ZrO_2$, $Nb_2O_5$, $P_2O_5$ and/or PbO in varying composition and varying proportions. Particular preference is given to high-refractive-index glass materials, such as flint glass and heavy flint glass.

Depending on the material employed, the substrate flakes which are suitable in accordance with the invention have a geometrical thickness in the range from 100 to 600 nm.

A prerequisite for suitability as pigment substrate is, in addition, that the substrates can be produced by synthetic means as planar flakes in the layer thickness desired in each case, which is, however, the case for the materials indicated. In addition, it is extremely advantageous if the pigment substrates employed in accordance with the invention are in crystalline form and particularly preferably in the form of single crystals.

In order to be able to obtain a green inherent interference of the substrate flakes, substrate flakes comprising $Al_2O_3$ or comprising $Al_2O_3$ with a content of up to 5% by weight of $TiO_2$, based on the weight of the substrate, and substrate flakes which comprise $Al_2O_3$ with a proportion of at least 90% by weight, based on the weight of the substrate, have a geometrical thickness in the range from 180 to 250 nm or from 350 to 450 nm.

Substrate flakes comprising $TiO_2$ or those which comprise $TiO_2$ with a proportion of at least 90% by weight, based on the weight of the substrate, have in accordance with the invention a geometrical thickness in the range from 110 to 170 nm or in the range from 240 to 310 nm.

For substrate flakes which consist of $ZrO_2$ or substrate flakes which comprise $ZrO_2$ with a proportion of at least 90% by weight, based on the weight of the substrate, the geometrical thickness of the substrate is in accordance with the invention between 140 and 210 nm or in the range from 260 to 400 nm.

Glass flakes which comprise a maximum of 70% by weight of $SiO_2$ have a geometrical thickness of 230 to 300 nm or of 400 to 470 nm.

The substrates employed are particularly preferably flakes comprising $Al_2O_3$ or comprising $Al_2O_3$ with a content of up to 5% by weight of $TiO_2$, based on the weight of the substrate, both of which are encompassed below by the term aluminium dioxide flakes, where the flakes have a geometrical thickness in the range from 180 to 250 nm, preferably in the range from 190 to 230 nm. As described below, these can be produced in the form of single crystals.

The standard deviation in the thickness of the individual substrate flakes here is preferably not more than 10%, based on the average of the respective substrate thickness. A relatively small thickness deviation of this type can be controlled via the respective production process.

The particle size of the substrate particles is comparatively small, since only finely divided particles can be employed in a very wide variety of print applications. It is in the range 5-40 µm. The $d_{50}$ value of the particle size distribution is in accordance with the invention in the range from 10 to 25 µm, preferably in the range from 15 to 20 µm, in particular in the range from 15 µm to <20 µm. The $d_{95}$ value of the particle size distribution is in accordance with the invention in the range from 35 to 40 µm, in particular from 35 µm to <40 µm. This is a narrow particle size distribution which can be adjusted via the process parameters in the production process and/or via additional grinding and/or classification steps. The particle size and the particle size distribution can be determined by various methods which are usual in the art. However, preference is given in accordance with the invention to the use of the laser diffraction method in a standard method by means of a Malvern Mastersizer 2000, APA200 (product from Malvern Instruments Ltd., UK). This method has the advantage that particle size and particle size distribution can be determined simultaneously under standard conditions.

The particle size and the thickness of individual particles can in addition be determined with the aid of SEM (scanning electron microscope) images. In the case of the latter, particle size and geometrical particle thickness can be determined by direct measurement. In order to determine average values, at least 1000 particles are evaluated individually and the results averaged.

The form factor of the support flakes, i.e. the ratio of length or width to thickness, is generally from 2:1 to 1.000:1, in particular from 5:1 to 500:1 and very particularly preferably from 20:1 to 300:1.

It is a particular advantage of the golden interference pigments in accordance with the present invention that, due to the smooth and planar surfaces of the synthetically produced substrates and due to the comparatively high refractive index to be ascribed to the substrate, it is possible to obtain lustre values which cannot be achieved with conventional interference pigments, for example based on mica, of the same size, even in the case of relatively small particle sizes of the substrates in the application medium.

The golden interference pigments according to the invention have at least one layer which comprises a mixture or mixed oxide of $Fe_2O_3$ and $TiO_2$ on the substrate, which has per se a green interference colour.

This layer preferably consists either of a mixture of $Fe_2O_3$ and $TiO_2$ or of a mixed oxide thereof, but may also, optionally, be composed of at least 80% by weight, in particular at least 90% by weight, of these, based on the weight of the substrate, and additionally of 10 to 20% by weight of further metal oxides, selected from $Al_2O_3$, $Ce_2O_3$, $B_2O_3$, $ZrO_2$ and $SnO_2$, either individually or in a mixture. The mixed oxide here is preferably pseudobrookite ($Fe_2TiO_5$). If a mixture of $Fe_2O_3$ and $TiO_2$ is present in the layer, the molar ratio of $Fe_2O_3$ to $TiO_2$ is from 1:4 to 4:1, preferably from 1:2 to 2:1.

In addition to the high refractive indices of the materials employed ($TiO_2$ (anatase) 2.5, $TiO_2$ (rutile) 2.7, haematite 2.9), a layer of this type also has yellow-brown to yellow-red inherent absorption.

The geometrical layer thickness of the layer comprising a mixture or mixed oxide of $Fe_2O_3$ and $TiO_2$ is in accordance with the invention in the range from 20 nm to 250 nm, in particular in the range from 50 nm to 150 nm.

As already described above, the refractive index difference Δn between substrate and layer located on the substrate is at least 0.1, in particular at least 0.2.

A layer which comprises a mixture or mixed oxide of $Fe_2O_3$ and $TiO_2$ is preferably located directly on the substrate.

However, particular preference is given to an embodiment of the present invention in which the golden interference pigment has two layers which comprise a mixture or mixed oxide of $Fe_2O_3$ and $TiO_2$.

In the latter case, the two layers, each comprising $Fe_2O_3$ and $TiO_2$, are separated from one another by at least one further layer comprising a colourless, dielectric material, i.e. the at least one further dielectric layer is in the form of an interlayer between the two layers each comprising $Fe_2O_3$ and $TiO_2$.

If only a single interlayer of this type is present, it is in accordance with the invention a layer comprising a colourless dielectric material which has a refractive index n of ≤1.8. A suitable material employed for this purpose is $SiO_2$, $Al_2O_3$, oxide hydrates thereof, mixtures thereof, or also $MgF_2$. The interlayer particularly preferably consists of $SiO_2$, the corresponding oxide hydrate, or a mixture thereof. The geometrical layer thickness of this layer is in accordance with the invention between 5 and 100 nm, in particular between 20 and 50 nm.

If more than one interlayer is present, where the number of interlayers is preferably 2 or 3, the second and optionally third interlayer present between the layers each comprising a mixture or mixed oxide of $Fe_2O_3$ and $TiO_2$ is additionally a layer which consists of a colourless dielectric material which has a refractive index n of >1.8. Particularly suitable for this purpose are colourless metal oxides, such as $TiO_2$ and $ZrO_2$, oxide hydrates of $TiO_2$ or $ZrO_2$, or mixtures of the oxide hydrates and the respective oxides, or materials which comprise $TiO_2$, $ZrO_2$ or the corresponding oxide hydrates in a proportion of at least 80% by weight, based on the weight of the layer, and may optionally comprise up to 20% by weight, based on the layer, of foreign oxides. Further constituents of the high-refractive-index transparent layer may be the oxides or oxide hydrates of Sn, Si, Ce, Al, Ca or Zn.

Preference is given to the use of $TiO_2$, which may be in the form either of the anatase modification or of the rutile modification. The generation of a rutile modification is familiar to the person skilled in the art and is described, for example, in the publications EP 271 767 B1, DE 25 22 572 C2 or U.S. Pat. No. 6,626,989.

The geometrical thickness of this (these) high-refractive-index layer(s) is in accordance with the invention in each case between 5 and 60 nm, in particular in the range from 10 to 60 nm, and particularly preferably in the range from 10 to 50 nm. The second and optionally third interlayers are located above or below the interlayer comprising a colourless dielectric material which has a refractive index n of ≤1.8 or on both sides of the latter.

However, the geometrical thickness of the totality of all interlayers is preferably not more than 100 nm, in particular not more than 50 nm.

In a particularly preferred embodiment of the present invention, at least one of the layers comprising a mixture or mixed oxide of $Fe_2O_3$ and $TiO_2$ is in the form of a pseudobrookite layer. Especial preference is given to an embodiment of the present invention in which both layers which comprise a mixture or mixed oxide of $Fe_2O_3$ and $TiO_2$ are in the form of a pseudobrookite layer, if two of these layers are present.

In a further embodiment of the present invention, a single layer is present which comprises a mixture or mixed oxide of $Fe_2O_3$ and $TiO_2$ and, instead of a second layer of the same type, a two-layer system comprising an $Fe_2O_3$ layer and a $TiO_2$ layer is present in the pigment according to the invention, including the above-mentioned interlayer(s). Due to the resultant multiplicity of layers, however, an embodiment of this type is not particularly preferred.

Both the layer(s) comprising a mixture or mixed oxide of $Fe_2O_3$ and $TiO_2$ and at least one of the interlayer(s) optionally present act as optically active interference layers and therefore contribute to the overall interference colour of the pigment according to the invention.

In particular, the following layer systems are suitable or preferred in accordance with the invention. The materials $SiO_2$ and $TiO_2$ used by way of example here for the respective layers comprising materials having a refractive index ≤1.8 or >1.8 may also be replaced by the materials mentioned above or also other suitable materials. All said layers preferably completely surround the flake-form support.

substrate (G)-$Fe_2O_3$/$TiO_2$
substrate (G)-$Fe_2TiO_5$
substrate (G)-$Fe_2O_3$/$TiO_2$—$SiO_2$—$Fe_2O_3$/$TiO_2$
substrate (G)-$Fe_2O_3$/$TiO_2$—$SiO_2$—$Fe_2TiO_5$
substrate (G)-$Fe_2TiO_5$—$SiO_2$—$Fe_2O_3$/$TiO_2$
substrate (G)-$Fe_2O_3$—$TiO_2$—$SiO_2$—$Fe_2O_3$/$TiO_2$
substrate (G)-$Fe_2O_3$/$TiO_2$—$SiO_2$—$Fe_2O_3$—$TiO_2$
substrate (G)-$Fe_2O_3$—$TiO_2$—$SiO_2$—$Fe_2TiO_5$
substrate (G)-$Fe_2TiO_5$—$SiO_2$—$Fe_2O_3$—$TiO_2$
substrate (G)-$Fe_2TiO_5$—$SiO_2$—$Fe_2TiO_5$
substrate (G)-$Fe_2O_3$/$TiO_2$—$SiO_2$—$TiO_2$—$Fe_2O_3$/$TiO_2$
substrate (G)-$Fe_2O_3$/$TiO_2$—$SiO_2$—$TiO_2$—$Fe_2TiO_5$
substrate (G)-$Fe_2TiO_5$—$SiO_2$—$TiO_2$—$Fe_2O_3$/$TiO_2$
substrate (G)-$Fe_2O_3$—$TiO_2$—$SiO_2$—$TiO_2$—$Fe_2O_3$/$TiO_2$
substrate (G)-$Fe_2O_3$/$TiO_2$—$SiO_2$—$TiO_2$—$Fe_2O_3$—$TiO_2$
substrate (G)-$Fe_2O_3$—$TiO_2$—$SiO_2$—$TiO_2$—$Fe_2TiO_5$
substrate (G)-$Fe_2TiO_5$—$SiO_2$—$TiO_2$—$Fe_2O_3$—$TiO_2$
substrate (G)-$Fe_2TiO_5$—$SiO_2$—$TiO_2$—$Fe_2TiO_5$
substrate (G)-$Fe_2O_3$/$TiO_2$—$TiO_2$—$SiO_2$—$Fe_2O_3$/$TiO_2$
substrate (G)-$Fe_2O_3$/$TiO_2$—$TiO_2$—$SiO_2$—$Fe_2TiO_5$
substrate (G)-$Fe_2TiO_5$—$TiO_2$—$SiO_2$—$Fe_2O_3$/$TiO_2$
substrate (G)-$Fe_2O_3$/$TiO_2$—$TiO_2$—$SiO_2$—$Fe_2O_3$—$TiO_2$
substrate (G)-$Fe_2TiO_5$—$TiO_2$—$SiO_2$—$Fe_2O_3$—$TiO_2$
substrate (G)-$Fe_2TiO_5$—$TiO_2$—$SiO_2$—$Fe_2TiO_5$
substrate (G)-$Fe_2O_3$/$TiO_2$—$TiO_2$—$SiO_2$—$TiO_2$—$Fe_2O_3$/$TiO_2$
substrate (G)-$Fe_2O_3$/$TiO_2$—$TiO_2$—$SiO_2$—$TiO_2$—$Fe_2TiO_5$
substrate (G)-$Fe_2TiO_5$—$TiO_2$—$SiO_2$—$TiO_2$—$Fe_2O_3$/$TiO_2$
substrate (G)-$Fe_2O_3$/$TiO_2$—$TiO_2$—$SiO_2$—$TiO_2$—$Fe_2O_3$—$TiO_2$
substrate (G)-$Fe_2TiO_5$—$TiO_2$—$SiO_2$—$TiO_2$—$Fe_2O_3$—$TiO_2$
substrate (G)-$Fe_2TiO_5$—$TiO_2$—$SiO_2$—$TiO_2$—$Fe_2TiO_5$ Of these, particular preference is given to the layer systems substrate (G)-$Fe_2TiO_5$
substrate (G)-$Fe_2TiO_5$—$SiO_2$—$Fe_2TiO_5$
substrate (G)-$Fe_2TiO_5$—$SiO_2$—$TiO_2$—$Fe_2TiO_5$
substrate (G)-$Fe_2TiO_5$—$TiO_2$—$SiO_2$—$Fe_2TiO_5$ and
substrate (G)-$Fe_2TiO_5$—$TiO_2$—$SiO_2$—$TiO_2$—$Fe_2TiO_5$.

Substrate (G) in each case denotes a transparent substrate flake having green inherent interference, as described above. $Fe_2O_3$/$TiO_2$ means a mixture of $Fe_2O_3$ and $TiO_2$.

In the golden interference pigments according to the invention, the substrate having the inherent interference colour "green" contributes in a particularly advantageous manner to the overall colour impression of the pigment. This is because the green interference colour of the substrate at the same time results in a red transmission colour of the substrate, which scatters on the respective application background, i.e., for example, on the print material in the case of print applications. In particular in the case of relatively thick application layers in which a plurality of pigments lie one above the other in the application medium, for example in the case of intaglio printing, the transmission colour "red" scattered in this way reinforces the reddish or reddish-yellow or brown-yellow absorption colour of the layer(s) comprising a mixture or mixed oxide of $Fe_2O_3$ and $TiO_2$ in an advantageous manner towards the desired yellow-red region. At the same time, the interference colour "green" of the substrate gives rise to a mixed colour with the interference colour of the coating, i.e. the interference colour of at least the layer which comprises a mixture or mixed oxide of $Fe_2O_3$ and $TiO_2$, and optionally the further interference layers present. If this interference colour of the coating is established in the region of a red or reddish interference, an overall interference in the yellow-golden colour region arises. Both the interference colour of the substrate and also the resultant transmission colour of the substrate thus cause reinforcement of the overall optical impression of the pigment according to the invention in the red-gold region, and do so independently of the viewing angle. At the same time, the golden interference pigments according to the invention, as already described above, have strong lustre in spite of their comparatively small particle sizes in the application medium. In addition, the hiding power and the colour saturation are in a suitable range which is particularly preferred for print applications.

The golden interference pigments according to the invention may be provided with an inorganic and/or organic, so-called post-coating on their outer surface in addition to the layers described above. This post-coating, which is usually used in the art, serves, for example, for simplification of incorporation into the application medium, for improvement of the weathering resistance, for reduction of the yellowing tendency of the application medium or for better distribution of the interference pigments in the application medium. Post-coatings have virtually no effect on the optical properties (colouristic properties) of the interference pigments and are present on the pigment surface with extremely small layer thicknesses, which are generally only in the region of molecular monolayers up to about 15 nm, preferably up to about 5 nm. Corresponding processes and materials are known in large number to the person skilled in the art and are described, for example, in the publications DE 22 15 191, DE 31 51 354, DE 32 35 017, DE 33 34 598, EP 0090259, EP 634 459, WO 96/32446, WO 99/57204 and WO 01/92425.

The present invention also relates to a process for the preparation of golden interference pigments in which a synthetically produced transparent substrate which has a green inherent interference colour is covered with at least one layer which comprises a mixture or mixed oxide of $Fe_2O_3$ and $TiO_2$.

Suitable synthetically produced substrates having a green inherent interference colour are the substrates already described above which are transparent and have a refractive index n in the range from >1.5 to 2.5 and in particular from 1.65 to 2.5, preferably substrate flakes which consist of $Al_2O_3$, of $Al_2O_3$ with a content of up to 5% by weight of $TiO_2$, based on the weight of the substrate, of $ZrO_2$ or of $TiO_2$, or substrate flakes which comprise $Al_2O_3$, $ZrO_2$ or $TiO_2$ with a proportion of at least 90% by weight, based on the weight of the substrate. Further constituents of the transparent substrate flakes may be the oxides or oxide hydrates of Sn, Si, Ce, Al, Ca or Zn, which, however, are present in the substrate at most with a proportion of 10% by weight, based on the weight of the substrate.

The glass flakes already described above which comprise up to 70% by weight of $SiO_2$ and further constituents are also suitable.

Depending on the material, the geometrical thicknesses of the substrates already described above must be complied with in order to be able to obtain a green inherent interference colour of the substrate flakes.

The flake-form substrates described above, essentially consisting of $Al_2O_3$, can preferably be produced here by the process described in EP 763 573 A2. These substrates comprise small amounts of $TiO_2$, which simplifies the subsequent coating with interference layers. The aluminium oxide flakes produced by this process are obtained as single crystals in a crystal-growth process, in which the particle size of the substrates and also their geometrical thickness, whose standard deviation is not greater than 10%, can be controlled by the process parameters. The corresponding influencing parameters are known to the person skilled in the art. If other foreign oxides are to be present instead of $TiO_2$, the procedure is analogous to the process described in EP 763 573 A2 with replacement of the raw materials. However, aluminium dioxide flakes in the form of hexagonal flakes having a particle diameter of greater than 10 μm and an aspect ratio (particle diameter/thickness) of 5 to 10, which are known from JP-A 111239/1982, or the hexagonal aluminium dioxide flakes described in JP-A 39362/1992 are also suitable.

Substrate flakes which consist entirely or predominantly of $ZrO_2$, $TiO_2$ oxide hydrates thereof or mixtures thereof can be produced analogously to the process described in WO 93/08237. However, the substrate flakes produced analogously to this process should not comprise any dissolved or undissolved colorants. They are produced from the corresponding, preferably inorganic, precursor material in a belt process, in which the precursor is applied to the belt, converted into the oxidic form or the oxide hydrate using acid, solidified and subsequently detached from the belt and optionally calcined. The geometrical layer thickness of the substrate flakes is adjusted via the application amount or wet-layer thickness of the precursor layer, which is possible very precisely and results in a narrow thickness distribution with variations of at most 10%. The particle size of the substrate flakes must be adjusted via subsequent grinding and classification processes, but these are usual in the art.

Flake-form glass substrates are commercially available from diverse suppliers in various thicknesses and qualities, for example borosilicate (ECR) glass flakes in thicknesses of 100 to 500 nm from Glassflake Australia Pty Ltd.

In the production process according to the invention, the covering of the flake-form substrates with the subsequent layer comprising $Fe_2O_3$ and $TiO_2$ and, where appropriate, all further interference layers of the layer system is preferably carried out in an aqueous dispersion by means of a wet-chemical process by hydrolytic decomposition of, in particular, inorganic metal salts.

The preparation of interference pigments by wet-chemical processes from inorganic starting materials is known per se. Mention may be made here by way of example of preparation processes which are usual in the art, as described in the patent specifications DE 14 67 468, DE 19 59 988, DE 20 09 566, DE 22 14, 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602 or DE 32 35 017.

To this end, the substrate flakes are suspended in water, and one or more hydrolysable metal salts are added at a pH which is suitable for hydrolysis, so that the metal oxide hydrates or metal oxides are precipitated onto the substrate flakes. The amount of the metal salts, the pH and the addition rate should advantageously be selected so that secondary precipitations do not occur. The pH is generally adjusted and kept constant at the same time during the precipitation by the addition of an acid and/or base. The pigments obtained are subsequently separated off, generally washed, dried and optionally calcined. The drying is usually carried out at temperatures between 50 and 150° C. for a period of 6 to 18 h, while the calcination process is carried out for a time depending on the respective layer structure and generally takes place at temperatures between 250 and 1100° C., preferably between 350 and 900° C.

If necessary, the calcined pigment is subsequently sieved.

The covering with various layers can be carried out in each case individually, where the pigment is dried after each covering step and optionally calcined and subsequently re-suspended, or in a one-pot process with only a single washing, drying and optionally calcination step at the end of the pigment preparation.

Suitable for the application of the interference layers are water-soluble inorganic starting materials or metal salts respectively which have long been familiar to the person skilled in the art for processes of this type, for example $FeCl_3$, $Fe(NO_3)_3$, $FeNH_4(SO_4)_2$, $Fe_2(SO_4)_3$ or $TiCl_4$ for the application of the layer which comprises a mixture or mixed oxide of $Fe_2O_3$ and $TiO_2$. These are preferably employed in aqueous solution. Particular preference is given to the use of $FeCl_3$ and $TiCl_4$.

In order to be able to precipitate a mixture or mixed oxide of $Fe_2O_3$ and $TiO_2$ directly onto the substrate flake, it is necessary to set the pH in the range from 1.5 to 4.0, preferably in the range from 2.0 to 3.0. The starting materials are for this purpose employed in the mixing ratio desired in each case. Otherwise, the general process description described above is followed. The reaction temperature is in the range between 50° C. and 100° C.

In a particularly preferred embodiment of the process according to the invention, two layers which comprise a mixture or mixed oxide of $Fe_2O_3$ and $TiO_2$ are applied to the flake-form substrate, where at least one further layer comprising a colourless dielectric material is applied between these layers, and the material for this further layer has a refractive index n of <1.8.

The material having a refractive index n of <1.8 um is preferably silicon dioxide, silicon dioxide hydrate or a mixture thereof. A layer of this type is referred to below as $SiO_2$ layer.

For the application of an $SiO_2$ layer, a sodium or potassium water-glass solution is generally employed. The precipitation of a silicon dioxide or silicon dioxide hydrate layer is carried out at a pH in the range from 6 to 10, preferably from 7 to 9.

The substrate already coated in advance with a layer which comprises a mixture or mixed oxide of $Fe_2O_3$ and $TiO_2$ is preferably suspended in water here, and the suspension is heated to a temperature in the range from 50 to 100° C. The pH is set in the range from 6 to 10 and kept constant by simultaneous addition of a dilute mineral acid, for example HCl, $HNO_3$ or $H_2SO_4$. A sodium or potassium water-glass solution is added to this suspension. As soon as the desired layer thickness of $SiO_2$ is obtained on the coated substrate, the addition of the silicate solution is stopped, and the batch is stirred for a further 0.5 hours.

Alternatively, a hydrolytic coating with $SiO_2$ can also be carried out using organic silicon compounds, such as, for example, TEOS, in an acid- or base-catalysed process via a sol-gel reaction. This is likewise a wet-chemical process.

In a further embodiment of the process according to the invention, at least one further layer which consists of a colourless dielectric material is additionally applied between the layers which comprise a mixture or mixed oxide of $Fe_2O_3$ and $TiO_2$, where the material has a refractive index n of >1.8. As already described above, this is preferably a $TiO_2$ layer, which is applied either directly to the first layer comprising a mixture or mixed oxide of $Fe_2O_3$ and $TiO_2$ and/or directly to the interlayer which consists of a material having a refractive index of ≤1.8.

The application of a $TiO_2$ layer is preferably carried out here analogously to the process described in U.S. Pat. No. 3,553,001. An aqueous titanium salt solution is slowly added here to a suspension of the pigment to be coated, the suspension is heated to 50 to 100° C., and the pH is kept virtually constant in the range from 0.5 to 5.0 by simultaneous addition of a base, for example an aqueous ammonium hydroxide solution or an aqueous alkali-metal hydroxide solution. When the desired $TiO_2$ layer thickness has been reached on the pigment flakes, the addition of the titanium salt solution and the base is stopped. Since the addition of the titanium salt solution is carried out so slowly that quasi-complete deposition of the hydrolysis product on the pigment flakes takes place, there are virtually no secondary precipitations. The process is known as a titration process.

The deposition of a second layer comprising a mixture or mixed oxide of $Fe_2O_3$ and $TiO_2$ is carried out analogously to the first layer of this type.

At least one of the layers which comprise a mixture or mixed oxide of $Fe_2O_3$ and $TiO_2$ is preferably a pseudobrookite layer, which either consists of pseudobrookite or comprises the latter in a proportion of at least 80%, preferably at least 90%, based on the weight of the layer. In particular, the golden interference pigment according to the invention has two layers of this type.

It should not remain unmentioned that the coating of the flake-form substrate described above with interference layers may alternatively also be carried out by gas-phase deposition by means of a fluidised-bed reactor. Use may be made here of the technologies described, for example, in EP 045 851 and EP 106 235. However, the wet-chemical processes described above are preferred.

The present invention also relates to the use of the said golden interference pigments in paints, coatings, printing inks, plastics, glasses, paper, ceramic, cosmetic formulations, for the laser marking of plastics or paper and for the preparation of pigment preparations and dry preparations. Pigment preparations and dry preparations here are taken to mean pigment pastes in water and/or organic solvents, optionally with addition of binders and assistants, or low-solvent or solvent-free preparations in the form of granules, pearlets, chips, pellets, briquettes, sausages, etc. The last-mentioned dry preparations in particular are preferably employed in print applications since they enable dust-free working.

In principle, the golden interference pigments in accordance with the present invention can thus be employed in all common applications in which effect pigments, in particular interference pigments, can usually be used.

They can be employed there as the sole colorant or alternatively also in a blend with inorganic or organic dyes or pigments, for example white, coloured or black pigments, with LCPs (liquid crystal pigments) and/or with other conventional effect pigments based on metallic or non-metallic substrates. All conceivable mixing ratios are possible here.

The specific application media may of course also comprise the generally conventional assistants and additives as well as binders, fillers and/or solvents, without the need to discuss these in greater detail here.

The proportion of the golden interference pigments according to the invention in the respective application medium is dependent on the specific application and can take place in a broad concentration range.

The application medium which can be employed is frequently coating compositions which are applied to the respective backgrounds, for example print materials, by means of conventional application methods, such as printing, spraying, knife coating, roller coating, brush coating, etc., dried and optionally additionally cured or crosslinked.

However, the present golden interference pigments are particularly suitable for printing processes, indeed for virtually all common printing processes. Particular mention may be made here of the gravure printing process, the flexographic printing process, the screen printing process, the intaglio printing process and the offset printing process.

Printing inks according to the invention which comprise the present golden interference pigment are therefore, in particular, gravure printing inks, flexographic printing inks, screen printing inks, intaglio printing inks or offset printing inks. These may comprise the interference pigment according to the invention in the conventional pigmentation, which is generally between 1 and 35% by weight, exceptionally up to 40% by weight, based on the weight of the printing ink.

All other printing ink constituents, such as binders, solvents, fillers, photoinitiators, curing agents, flow retardants, wetting agents, drying agents, etc., to mention but a few which are usually used in the art, may of course likewise be present in the respective printing inks in the concentrations usually conventional at the same time with the golden interference pigment according to the invention. With respect to the pigment-free semi- and finished products which can be employed, the conventional printing ink vehicles from the manufacturers established on the market can be used.

Of particular importance is the use of the pigments according to the invention in printing processes which, for various reasons, can only work with very finely divided pigments. Mention may be made here, in particular, of the offset printing process and the intaglio printing process (engraved steel printing process using paste-form, high-viscosity printing inks).

The interference pigments according to the invention meet the requirement for the finely divided nature of the pigments to be employed here without the need to accept disadvantages in relation to the lustre, the colour saturation or the desired warm gold shade of the resultant prints. They can be used in the conventional pigment concentrations for the said processes and in combination with the other common ingredients of suitable printing ink vehicles or printing inks. In addition, the interference pigments according to the invention are capable of aligning well on the print material in spite of their finely divided nature and having high colour saturation in the red-gold region in the print image, even if the print layer produced, as in the offset printing process, is only up to a maximum of 3 microns thin.

The interference pigments according to the invention do not clog the printing plates (for example engravings in printing plates and cylinders) and the supply lines and therefore ensure clean print images and good production-printing behaviour in the mass production of print products. In addition, they are very chemically and mechanically stable, so that the strongly basic wiping solutions employed, for example, in the intaglio printing process have no adverse effects on the optical characteristics of the pigments according to the invention.

The golden interference pigments in accordance with the present invention are therefore particularly suitable for use in most conventional, inexpensive printing and coating processes and serve for the production of gold prints and gold decorations both in the packaging sector and also in the decorative sector and in particular also in the security sector, where they can advantageously be employed, for example, for the production of bank notes and other documents of value using the specific coating processes which are usual there, for example the intaglio printing process. In the screen printing process, which is widely used industrially for the printing of textiles and paper, the use of screens with narrower meshes and thus the printing of finer lines in a saturated red-gold hue is possible.

The present invention will be explained in greater detail with reference to the following examples, but is not intended to be restricted thereto.

EXAMPLE 1

200 g of aluminium dioxide flakes having a green interference colour which have a particle size distribution $d_{50}$=18-19.5 µm and $d_{95}$=37-39 µm (determined using Malvern Mastersizer 2000) and a geometrical thickness of about 220 nm (determined by SEM) are suspended in 2 l of demineralised water, and the suspension is heated to a temperature of 75° C. When this temperature has been reached, a solution of 248.0 g of $FeCl_3 \times 6H_2O$, 87.0 g of $TiCl_4$ and 10.4 g of $AlCl_3 \times 6 H_2O$ in 291.2 g of demineralised water is slowly metered in with stirring. The pH of the suspension is kept constant at 2.6 using NaOH solution (32%). After addition of the metal salt solutions, the mixture is stirred for about a further 15 minutes. The pH is subsequently increased to pH 7.5 using NaOH solution (32%), and 592.6 g of sodium water-glass solution (13.5% of $SiO_2$) are slowly added at this pH. The pH is then reduced to 2.0 using hydrochloric acid (10% of HCl), and the mixture is stirred for a further 15 minutes. 192 ml of $TiCl_4$ solution (370 g of $TiCl_4$/l) are subsequently metered in, while the pH is kept constant using NaOH solution (32%). The pH is subsequently increased to 2.6 using NaOH solution (32%), and 264.8 g of $FeCl_3 \times 6 H_2O$, 92.6 g of $TiCl_4$ and 11.0 g of $AlCl_3 \times 6 H_2O$ in 133.6 g of demineralised water are slowly metered in at this value. The pH is kept constant using NaOH solution (32%). The mixture is subsequently stirred for a further 15 minutes, the pH is increased to pH 5.0 (NaOH solution, 32%), and the mixture is stirred for a further 15 minutes. The pigment is filtered, washed with demineralised water and dried at 110° C. It is subsequently calcined at 850° C. for 30 minutes.

A gold-coloured lustre pigment having a red-golden interference colour and mass tone, strong lustre and very good hiding power is obtained.

COMPARATIVE EXAMPLE 1

100 g of mica flakes having a particle size of 10-60 µm are suspended in 2 l of demineralised water, and the suspension is heated to a temperature of 75° C. When this temperature has been reached, a solution of 130.5 g of $FeCl_3 \times 6H_2O$, 46.5 g of $TiCl_4$ and 11.6 g of $AlCl_3 \times 6 H_2O$ in 84.3 g of demineralised water is slowly metered in with stirring. The pH of the suspension is kept constant at 2.6 using NaOH solution (32%). After addition of the metal salt solutions, the mixture is stirred for about a further 15 minutes. The pH is subsequently increased to pH 7.5 using NaOH solution (32%), and 431 g of sodium water-glass solution (13.5% of $SiO_2$) are slowly added at this pH. The pH is then reduced to 2.0 using hydrochloric acid (10% of HCl), and the mixture is stirred for a further 15 minutes. 393 g of $TiCl_4$ solution (370 g of $TiCl_4$/l) are subsequently metered in, while the pH is kept constant using NaOH solution (32%). The pH is subsequently increased to 2.6 using NaOH solution (32%), and 48.6 g of $FeCl_3 \times 6\ H_2O$, 18.6 g of $TiCl_4$ and 4.0 g of $AlCl_3 \times 6\ H_2O$ in 31.4 g of demineralised water are slowly metered in at this value. The pH is kept constant using NaOH solution (32%). The mixture is subsequently stirred for a further 15 minutes, the pH is increased to pH 5.0 (NaOH solution, 32%), and the mixture is stirred for a further 15 minutes. The pigment is filtered, washed with demineralised water and dried at 110° C. It is subsequently calcined at 850° C. for 30 minutes.

A gold-coloured lustre pigment having a golden interference colour, strong lustre, extremely high brightness and good hiding power is obtained.

Black/white paint cards are prepared from each of the gold pigments according to Example 1 and Comparative Example 1. The corresponding CIEL,a,b values are determined using an ETA device (STEAG-ETA Optic GmbH Inc.).

| Sample 75°/95° | | | | | |
|---|---|---|---|---|---|
| Black background | | | Chroma | Hue angle | Hiding |
| L | a | b | *C | *h | power |
| Ex. 1    117.8 | 19.8 | 96.4  | 98.4  | 78.4 | 35.8 |
| Comp. Ex. 158.9 | 4.3 | 104.0 | 104.1 | 87.6 | 30.8 |

The values shown above show that the pigment according to the invention according to Example 1 has high brightness, a very good chroma value and extremely high hiding power. In addition, it exhibits a significantly more reddish hue at a hue angle of about 78° than the comparative pigment at a hue angle of about 87°. By contrast, the comparative pigment has such high brightness that a gleaming yellow shade, but not a warm red-gold shade is perceived with the naked eye. By contrast, the hiding power of the comparative pigment remains significantly behind that of the pigment according to the invention according to Example 1. In addition, the pigment in accordance with Comparative Example 1 is not suitable for applications which require very finely divided pigments owing to the comparatively large particle size.

(In the CIELab system, the saturation of a colour is only described inadequately and is often equated with the chroma. According to Eva Lübbe, Sättigung im CIELAB-Farbsystem and LSh-Farbsystem [Saturation in the CIELAB Colour System and LSh Colour System)] Books on Demand GmbH, Norderstedt, 3rd Edition 2011, p. 47, the saturation of a colour is, however, better characterised by the ratio of the chroma of the colour to the overall colour impression. Accordingly, the saturation S is calculated as follows:

$$S = \frac{C^*_{ab}}{\sqrt{L^{*2} - C^{*2}_{ab}}} \cdot 100\%$$

where S represents the newly calculated saturation, L* represents the CIELAB lightness value and $C^*_{ab}$ represents the CIELAB chromaticity.

If the saturation of the samples according to Example 1 and the comparative example are calculated in accordance with the formula indicated, a value for the saturation of about 64% is obtained for Example 1, while the saturation in the comparative example is only about 55%. These values correspond to the visual perception, which gives a significantly higher colour saturation for the paint card of Example 1 than for that of the comparative example.)

Use Examples:
1. Intaglio Printing Ink:

| | |
|---|---|
| Gold pigment according to Example 1 | 15% by weight |
| Intaglio Varnish Flop 670179 | 85% by weight |

(Gleitsmann Security Inks)

The gold pigment is incorporated into the binder system under gentle conditions and printed onto paper using an engraved steel printing plate warmed to 40° C. to 70° C. A raised pattern of fine lines with a warm, red-golden hue in good saturation is obtained.

2. Offset Ink:
a)

| | |
|---|---|
| Gold pigment according to Example 1 | 15% by weight |
| OF printing varnish 96147 | 85% by weight |

(Jaenecke and Schneemann Druckfarbe GmbH)
b)

| | |
|---|---|
| Gold pigment according to Example 1 | 30% by weight |
| OF printing varnish 96147 | 70% by weight |

(Jaenecke and Schneemann Druckfarbe GmbH)

The gold pigment is in each case incorporated into the printing ink vehicle under gentle conditions, and the printing ink obtained is printed. In both cases, a readily visible, strikingly red-golden pattern is obtained, whose perceptible colour saturation appears significantly stronger in the case of the print result in accordance with 2b than in the case of the print result according to Example 2a.

3. Screen Printing Ink:

The gold pigment according to Example 1 is introduced in proportions of 10% by weight or 15% by weight in each case into 90% by weight or 85% by weight in each case of screen printing binder (AquaJet FGLM 093 or MZ Lack 093, Pröll KG, or UV-aqueous 672048, Gleitsmann Security Inks) under gentle conditions. The printing is carried out using commercially available screens (61-64 or 77-55).

The printing inks obtained can be printed successfully with each of the screens without clogging the screens. Saturated, red-golden, highly opaque print images with high lustre are obtained in each concentration and with each of the binders indicated.

4. Gravure Printing Ink/Flexographic Printing Ink:

The gold pigment according to Example 1 is incorporated in proportions of 15% by weight or 25% by weight in each case into 85% by weight or 75% by weight in each case of gravure/flexographic printing binder (NC TOB OPV-00, Siegwerk, or Haptobond CT 105, Hartmann Druckfarben GmbH/Sun Chemical) under gentle conditions with stirring. The viscosity of the printing ink is adjusted using small amounts of solvent.

The print images obtained exhibit a saturated red-gold hue and high lustre.

The invention claimed is:

1. Golden interference pigment which comprises a flake-form substrate and at least one layer located on the substrate, wherein the flake-form substrate is a synthetically produced transparent substrate which has a green inherent interference colour, where the flake-form substrate consists of $Al_2O_3$ or consists of $Al_2O_3$ with a content of up to 5% by weight of $TiO_2$, based on the weight of the substrate, or comprises $Al_2O_3$ with a proportion of at least 90% by weight, based on the weight of the substrate, and has a geometrical thickness of 180 to 250 nm or 350 to 450 nm, or the flake-form substrate consists of $ZrO_2$ or comprises $ZrO_2$ with a proportion of at least 90% by weight, based on the weight of the substrate, and has a geometrical thickness of 140 to 210 nm or 260 to 400 nm, or the flake-form substrate consists of $TiO_2$ or comprises $TiO_2$ with a proportion of at least 90% by weight, based on the weight of the substrate, and has a geometrical thickness of 110 to 170 nm or 240 to 310 nm, or the flake-form substrate is a glass flake which comprises a maximum of 70% by weight of $SiO_2$ and has a geometrical thickness of 230 to 300 nm or 400to 470 nm, and at least one layer which comprises a mixture or mixed oxide of $Fe_2O_3$ and $TiO_2$ is located on the substrate, and the substrate has a particle size of 5-40 µm with a $d_{95}$ value of 35 µm to <40 µm.

2. Interference pigment according to claim 1, wherein the pigment has two layers which comprise a mixture or mixed oxide of $Fe_2O_3$ and $TiO_2$.

3. Interference pigment according to claim 2, which interference pigment has at least one further layer comprising a colourless dielectric material, which has a refractive index n of <1.8, and is present between the layers which comprise a mixture or mixed oxide of $Fe_2O_3$ and $TiO_2$.

4. Interference pigment according to claim 3, wherein a further layer comprising a colourless dielectric material, which has a refractive index n of >1.8, and is additionally present between the layers which comprise a mixture or mixed oxide of $Fe_2O_3$ and $TiO_2$.

5. Interference pigment according to claim 1, wherein the layer which comprises a mixture or mixed oxide of $Fe_2O_3$ and $TiO_2$ has a geometrical layer thickness of 30 nm to 180 nm.

6. Interference pigment according to claim 1, wherein at least one of the layers which comprise a mixture or mixed oxide of $Fe_2O_3$ and $TiO_2$ is a pseudobrookite layer.

7. A process for preparing a golden interference pigment according to claim 1, comprising covering the synthetically produced transparent substrate which has a green inherent interference colour, where the flake-form substrate consists of $Al_2O_3$ or consists of $Al_2O_3$ with a content of up to 5% by weight of $TiO_2$, based on the weight of the substrate, or comprises $Al_2O_3$ with a proportion of at least 90% by weight, based on the weight of the substrate, and has a geometrical thickness of 180 to 250 nm or 350 to 450 nm, or the flake-form substrate consists of $ZrO_2$ or comprises $ZrO_2$ with a proportion of at least 90% by weight, based on the weight of the substrate, and has a geometrical thickness of 140 to 210 nm or 260 to 400 nm, or the flake-form substrate consists of $TiO_2$ or comprises $TiO_2$ with a proportion of at least 90% by weight, based on the weight of the substrate, and has a geometrical thickness of 110 to 170 nm or 240 to 310 nm, or the flake-form substrate is a glass flake which comprises a maximum of 70% by weight of $SiO_2$ and has a geometrical thickness of 230 to 300 nm or 400 to 470 nm, and the substrate has a particle size of 5-40 µm with a $d_{95}$ value of 35 µm to <40 µm, with at least one layer which comprises a mixture or mixed oxide of $Fe_2O_3$ and $TiO_2$.

8. The process according to claim 7, wherein the covering is carried out in an aqueous dispersion by a wet-chemical process by hydrolytic decomposition of inorganic metal salts.

9. The process according to claim 7, wherein two layers which comprise a mixture or mixed oxide of $Fe_2O_3$ and $TiO_2$ are applied, where at least one further layer comprising a colourless dielectric material is applied between these layers, where the material for the further layer has a refractive index n of <1.8.

10. The process according to claim 9, wherein at least one further layer which consists of a colourless dielectric material, which has a refractive index n of >1.8, is additionally applied between the layers which comprise a mixture or mixed oxide of $Fe_2O_3$ and $TiO_2$.

11. The process according to claim 7, wherein at least one of the layers which comprise a mixture or mixed oxide of $Fe_2O_3$ and $TiO_2$ is a pseudobrookite layer.

12. A method for preparing a product selected from the group consisting of paints, coatings, printing inks, plastics, glasses, paper, ceramic, cosmetic formulations, laser marking of plastics, laser marking of paper, pigment preparations and dry preparations, comprising incorporating an interference pigment of claim 1 into said product.

13. The method according to claim 12, wherein the printing ink is a gravure printing ink, a flexographic printing ink, a screen printing ink, an intaglio printing ink or an offset printing ink.

14. A gravure printing ink, flexographic printing ink, screen printing ink, intaglio printing ink or offset printing ink comprising interference pigments according to claim 1.

15. Interference pigment according to claim 1, wherein the flake-form substrate consists of $Al_2O_3$ or consists of $Al_2O_3$ with a content of up to 5% by weight of $TiO_2$, based on the weight of the substrate, or comprises $Al_2O_3$ with a proportion of at least 90% by weight, based on the weight of the substrate, and has a geometrical thickness of 180 to 250 nm or 350 to 450 nm.

16. Interference pigment according to claim 1, wherein the flake-form substrate consists of $ZrO_2$ or comprises $ZrO_2$ with a proportion of at least 90% by weight, based on the weight of the substrate, and has a geometrical thickness of 140 to 210 nm or 260 to 400 nm.

17. Interference pigment according to claim 1, wherein the flake-form substrate consists of $TiO_2$ or comprises $TiO_2$ with a proportion of at least 90% by weight, based on the weight of the substrate, and has a geometrical thickness of 110 to 170 nm or 240 to 310 nm.

18. Interference pigment according to claim 1, wherein the flake-form substrate is a glass flake which comprises a maximum of 70% by weight of $SiO_2$ and has a geometrical thickness of 230 to 300 nm or 400 to 470 nm.

19. Interference pigment according to claim 1, wherein the substrate has a $d_{50}$ value of 15 μm to <20 μm.

20. An intaglio printing ink comprising interference pigments according to claim 1.

* * * * *